(12) United States Patent
Baker

(10) Patent No.: US 12,138,188 B2
(45) Date of Patent: Nov. 12, 2024

(54) SINGLE MEMBER INTRALUMINAL DEVICE AND METHOD OF FIXATION

(71) Applicant: BFKW, LLC, Ada, MI (US)

(72) Inventor: Randal S. Baker, Grand Rapids, MI (US)

(73) Assignee: BFKW, LLC, Ada, MI (US)

( * ) Notice: Subject to any disclaimer, the term of this patent is extended or adjusted under 35 U.S.C. 154(b) by 548 days.

(21) Appl. No.: 17/436,935

(22) PCT Filed: Mar. 11, 2020

(86) PCT No.: PCT/IB2020/052169
§ 371 (c)(1),
(2) Date: Sep. 7, 2021

(87) PCT Pub. No.: WO2020/183399
PCT Pub. Date: Sep. 17, 2020

(65) Prior Publication Data
US 2022/0168126 A1    Jun. 2, 2022

Related U.S. Application Data

(60) Provisional application No. 62/823,292, filed on Mar. 25, 2019, provisional application No. 62/816,629, filed on Mar. 11, 2019.

(51) Int. Cl.
*A61F 5/00* (2006.01)
(52) U.S. Cl.
CPC ................. *A61F 5/0076* (2013.01)
(58) Field of Classification Search
CPC .... A61F 5/0076; A61F 5/0036; A61F 5/0069; A61F 5/0013; A61F 5/004; A61F 5/0079;
(Continued)

(56) References Cited

U.S. PATENT DOCUMENTS

| 4,403,604 A | 9/1983 | Wilkinson et al. |
| 4,607,618 A | 8/1986 | Angelchik |

(Continued)

FOREIGN PATENT DOCUMENTS

| CN | 108938163 A | 12/2018 | |
| CN | 109984778 A * | 7/2019 | ............. A61B 17/00 |

(Continued)

OTHER PUBLICATIONS

"Obesity: Super-Sized Medical Device Market", Start-Up, Mar. 2003, Technology Strategies (Long Article), pp. 1-10 and a cover page.

(Continued)

*Primary Examiner* — Leslie A Lopez
*Assistant Examiner* — Quynh Dao Le
(74) *Attorney, Agent, or Firm* — Gardner, Linn, Burkhart & Ondersma LLP

(57) ABSTRACT

An intraluminal device and method of deploying an intraluminal device in a portion of a lumen includes the device having a body with a wall defining a surface. The surface is configured to a portion of a lumen. An anchor system made up of a plurality of anchors fixes the body to an inner wall of the lumen. At least intermittent pressure with the surface to the inner wall of the lumen. A tissue fold of the inner wall of the lumen is formed. Thee tissue fold is adjacent the body wall and transmits a force between the inner wall of the lumen and the device body.

15 Claims, 9 Drawing Sheets

(58) Field of Classification Search
CPC ...... A61F 5/003; A61F 5/0086; A61F 5/0089;
A61F 2/848; A61F 2002/045; A61F
2002/044; A61F 2002/9511; A61F
2002/8483; A61F 2220/0016; A61F
2220/0008; A61F 2220/0033; A61F 2/07;
A61F 2/04; A61F 2/90; A61H 1/00;
A61B 1/273; A61B 17/0401; A61B
17/1114; A61B 17/0487; A61B 17/064;
A61B 17/068; A61B 2017/00818; A61B
2017/0417; A61B 2017/0419; A61B
2017/0409; A61B 2017/0454; A61J
15/003
USPC .............. 604/8, 909; 623/23.65, 23.7, 23.64;
606/151, 191, 192
See application file for complete search history.

(56) References Cited

U.S. PATENT DOCUMENTS

| | | |
|---|---|---|
| 5,234,454 A | 8/1993 | Bangs |
| 5,306,300 A | 4/1994 | Berry |
| 5,366,504 A | 11/1994 | Andersen et al. |
| 5,507,755 A | 4/1996 | Gresl et al. |
| 5,662,713 A | 9/1997 | Andersen et al. |
| 5,741,279 A | 4/1998 | Gordon et al. |
| 5,820,584 A | 10/1998 | Crabb |
| 6,146,416 A | 11/2000 | Andersen et al. |
| 6,264,700 B1 | 7/2001 | Kilcoyne et al. |
| 6,280,415 B1 | 8/2001 | Johnson |
| 6,312,437 B1 | 11/2001 | Kortenbach |
| 6,355,070 B1 | 3/2002 | Andersen et al. |
| 6,398,802 B1 | 6/2002 | Yee |
| 6,432,040 B1 | 8/2002 | Meah |
| 6,447,533 B1 | 9/2002 | Adams |
| 6,468,298 B1 | 10/2002 | Pelton |
| 6,544,291 B2 | 4/2003 | Taylor |
| 6,558,400 B2 | 5/2003 | Deem et al. |
| 6,572,627 B2 | 6/2003 | Gabbay |
| 6,656,194 B1 | 12/2003 | Gannoe et al. |
| 6,675,809 B2 | 1/2004 | Stack et al. |
| 6,736,828 B1 | 5/2004 | Adams et al. |
| 6,740,121 B2 | 5/2004 | Geitz |
| 6,746,460 B2 | 6/2004 | Gannoe et al. |
| 6,755,869 B2 | 6/2004 | Geitz |
| 6,773,440 B2 | 8/2004 | Gannoe et al. |
| 6,800,081 B2 | 10/2004 | Parodi |
| 6,802,868 B2 | 10/2004 | Silverman et al. |
| 6,845,776 B2 | 1/2005 | Stack et al. |
| 6,916,332 B2 | 7/2005 | Adams |
| 6,960,233 B1 | 11/2005 | Berg et al. |
| 6,981,978 B2 | 1/2006 | Gannoe |
| 6,994,095 B2 | 2/2006 | Burnett |
| 6,994,715 B2 | 2/2006 | Gannoe et al. |
| 7,025,791 B2 | 4/2006 | Levine et al. |
| 7,033,373 B2 | 4/2006 | de la Torre et al. |
| 7,033,384 B2 | 4/2006 | Gannoe et al. |
| 7,037,344 B2 | 5/2006 | Kagan et al. |
| 7,044,979 B2 | 5/2006 | Silverman et al. |
| 7,066,945 B2 | 6/2006 | Hashiba et al. |
| 7,083,629 B2 | 8/2006 | Weller et al. |
| 7,083,630 B2 | 8/2006 | DeVries et al. |
| 7,087,088 B2 | 8/2006 | Berg et al. |
| 7,097,650 B2 | 8/2006 | Weller et al. |
| 7,097,665 B2 | 8/2006 | Stack et al. |
| 7,111,627 B2 | 9/2006 | Stack et al. |
| 7,146,984 B2 | 12/2006 | Stack et al. |
| 7,152,607 B2 | 12/2006 | Stack et al. |
| 7,167,750 B2 | 1/2007 | Knudson et al. |
| 7,211,114 B2 | 5/2007 | Bessler et al. |
| 7,220,284 B2 | 5/2007 | Kagan et al. |
| 7,232,461 B2 | 6/2007 | Ramer |
| 7,347,875 B2 | 3/2008 | Levine et al. |
| 7,431,725 B2 | 10/2008 | Stack et al. |
| 7,445,010 B2 | 11/2008 | Kugler et al. |
| 7,449,024 B2 | 11/2008 | Stafford |
| 7,678,068 B2 | 3/2010 | Levine et al. |
| 7,682,330 B2 | 3/2010 | Meade et al. |
| 7,704,264 B2 | 4/2010 | Ewers et al. |
| 7,708,752 B2 | 5/2010 | Durgin |
| 7,753,870 B2 | 7/2010 | Demarais et al. |
| 7,771,382 B2 | 8/2010 | Levine et al. |
| 7,794,447 B2 | 9/2010 | Dann et al. |
| 7,815,589 B2 | 10/2010 | Meade et al. |
| 7,815,591 B2 | 10/2010 | Levine et al. |
| 7,846,174 B2 | 12/2010 | Baker et al. |
| 7,922,650 B2 | 4/2011 | McWeeney et al. |
| 7,976,488 B2 | 7/2011 | Levine et al. |
| 7,981,163 B2 | 7/2011 | Meade et al. |
| 8,029,455 B2 | 10/2011 | Stack et al. |
| 8,043,355 B2 | 10/2011 | Shin et al. |
| 8,100,931 B2 | 1/2012 | Baker et al. |
| 8,137,301 B2 | 3/2012 | Levine et al. |
| 8,142,513 B2 | 3/2012 | Shalon et al. |
| 8,162,871 B2 | 4/2012 | Levine et al. |
| 8,182,459 B2 * | 5/2012 | Dann ................ A61F 5/0076 604/909 |
| 8,252,009 B2 | 8/2012 | Weller |
| 8,282,598 B2 | 10/2012 | Belhe et al. |
| 8,372,087 B2 | 2/2013 | Baker et al. |
| 8,447,403 B2 | 5/2013 | Sharma et al. |
| 8,506,477 B2 | 8/2013 | Waller et al. |
| 8,529,431 B2 | 9/2013 | Baker et al. |
| 8,556,956 B2 | 10/2013 | Cully et al. |
| 8,672,831 B2 | 3/2014 | Baker et al. |
| 8,721,528 B2 | 5/2014 | Ho et al. |
| 8,778,011 B2 | 7/2014 | Ryan |
| 8,784,436 B2 | 7/2014 | Ho et al. |
| 8,801,599 B2 | 8/2014 | Baker et al. |
| 8,894,670 B2 | 11/2014 | Baker et al. |
| 9,055,998 B2 | 6/2015 | Baker |
| 9,060,844 B2 | 6/2015 | Kagan et al. |
| 9,107,742 B2 | 8/2015 | Cully et al. |
| 9,198,789 B2 | 12/2015 | Baker et al. |
| 9,375,338 B2 | 6/2016 | Baker et al. |
| 9,414,948 B2 | 8/2016 | Baker et al. |
| 9,451,960 B2 * | 9/2016 | Huntley ............... A61F 5/0079 |
| 9,545,326 B2 | 1/2017 | Baker et al. |
| 9,549,833 B2 | 1/2017 | McHugo |
| 9,629,733 B2 | 4/2017 | Roeder |
| 9,839,545 B2 | 12/2017 | Baker et al. |
| 9,872,787 B2 | 1/2018 | Baker et al. |
| 10,182,901 B2 | 1/2019 | Baker et al. |
| 10,271,940 B2 | 4/2019 | Baker et al. |
| 2001/0011543 A1 | 8/2001 | Forsell |
| 2001/0020189 A1 | 9/2001 | Taylor |
| 2002/0032487 A1 | 3/2002 | Dua et al. |
| 2002/0091395 A1 | 7/2002 | Gabbay |
| 2003/0040804 A1 | 2/2003 | Stack et al. |
| 2003/0040808 A1 | 2/2003 | Stack et al. |
| 2003/0065359 A1 | 4/2003 | Weller et al. |
| 2003/0109935 A1 | 6/2003 | Geitz |
| 2003/0199989 A1 | 10/2003 | Stack et al. |
| 2003/0212450 A1 | 11/2003 | Schlick |
| 2004/0044357 A1 | 3/2004 | Gannoe et al. |
| 2004/0073222 A1 * | 4/2004 | Koseki ............... A61B 17/0642 606/75 |
| 2004/0087976 A1 | 5/2004 | DeVries et al. |
| 2004/0092892 A1 | 5/2004 | Kagan et al. |
| 2004/0106987 A1 | 6/2004 | Palasis et al. |
| 2004/0116999 A1 | 6/2004 | Ledergerber |
| 2004/0117031 A1 | 6/2004 | Stack et al. |
| 2004/0122456 A1 | 6/2004 | Vahid |
| 2004/0138761 A1 | 7/2004 | Stack et al. |
| 2004/0143342 A1 | 7/2004 | Stack et al. |
| 2004/0147958 A1 * | 7/2004 | Lam ................... A61B 17/3478 606/232 |
| 2004/0148034 A1 | 7/2004 | Kagan et al. |
| 2004/0172141 A1 | 9/2004 | Stack et al. |
| 2004/0210111 A1 | 10/2004 | Okada |
| 2004/0220682 A1 | 11/2004 | Levine et al. |
| 2005/0004582 A1 | 1/2005 | Edoga et al. |
| 2005/0043683 A1 | 2/2005 | Ravo |

(56) References Cited

U.S. PATENT DOCUMENTS

| | | |
|---|---|---|
| 2005/0080395 A1 | 4/2005 | Levine et al. |
| 2005/0096728 A1 | 5/2005 | Ramer |
| 2005/0125020 A1 | 6/2005 | Meade et al. |
| 2005/0177181 A1 | 8/2005 | Kagan |
| 2005/0192599 A1 | 9/2005 | Demarais |
| 2005/0192629 A1 | 9/2005 | Saadat et al. |
| 2005/0197715 A1 | 9/2005 | Kugler et al. |
| 2005/0203548 A1 | 9/2005 | Weller et al. |
| 2005/0228504 A1 | 10/2005 | Demarais |
| 2005/0245788 A1 | 11/2005 | Gerber |
| 2005/0245957 A1 | 11/2005 | Starkebaum et al. |
| 2005/0247320 A1 | 11/2005 | Stack et al. |
| 2005/0250980 A1* | 11/2005 | Swanstrom ........ A61B 17/0401 623/23.65 |
| 2005/0251165 A1 | 11/2005 | Vaughan et al. |
| 2005/0251176 A1 | 11/2005 | Swanstrom et al. |
| 2005/0283235 A1 | 12/2005 | Kugler et al. |
| 2006/0020277 A1 | 1/2006 | Gostout et al. |
| 2006/0036293 A1 | 2/2006 | Whitehurst et al. |
| 2006/0064120 A1 | 3/2006 | Levine et al. |
| 2006/0074473 A1 | 4/2006 | Gertner |
| 2006/0089571 A1 | 4/2006 | Gertner |
| 2006/0142844 A1 | 6/2006 | Lowe et al. |
| 2006/0149307 A1 | 7/2006 | Durgin |
| 2006/0155375 A1 | 7/2006 | Kagan et al. |
| 2006/0161139 A1 | 7/2006 | Levine et al. |
| 2006/0190019 A1 | 8/2006 | Gannoe et al. |
| 2006/0247721 A1 | 11/2006 | Maschino et al. |
| 2006/0253131 A1 | 11/2006 | Wolniewicz, III |
| 2006/0253142 A1 | 11/2006 | Bjerken |
| 2006/0253191 A1 | 11/2006 | Salahieh et al. |
| 2006/0264699 A1 | 11/2006 | Gertner |
| 2006/0265082 A1 | 11/2006 | Meade et al. |
| 2007/0005147 A1 | 1/2007 | Levine et al. |
| 2007/0010866 A1 | 1/2007 | Dann et al. |
| 2007/0010875 A1 | 1/2007 | Trout et al. |
| 2007/0088428 A1 | 4/2007 | Teichman |
| 2007/0112409 A1 | 5/2007 | Wu et al. |
| 2007/0123994 A1 | 5/2007 | Ortiz et al. |
| 2007/0166396 A1 | 7/2007 | Badylak et al. |
| 2007/0179590 A1 | 8/2007 | Lu et al. |
| 2007/0198035 A1 | 8/2007 | Threlkeld |
| 2007/0208360 A1 | 9/2007 | Demarias et al. |
| 2007/0208429 A1 | 9/2007 | Leahy |
| 2007/0233221 A1 | 10/2007 | Raju |
| 2007/0260112 A1 | 11/2007 | Rahmani |
| 2007/0270742 A1 | 11/2007 | Guetty |
| 2007/0276432 A1 | 11/2007 | Stack et al. |
| 2007/0293716 A1 | 12/2007 | Baker et al. |
| 2008/0015523 A1 | 1/2008 | Baker |
| 2008/0015618 A1 | 1/2008 | Sonnenschein et al. |
| 2008/0015633 A1 | 1/2008 | Abbott et al. |
| 2008/0065122 A1 | 3/2008 | Stack et al. |
| 2008/0065136 A1 | 3/2008 | Young |
| 2008/0215076 A1 | 9/2008 | Baker |
| 2008/0312678 A1 | 12/2008 | Pasricha |
| 2009/0018389 A1 | 1/2009 | Laufer et al. |
| 2009/0030435 A1* | 1/2009 | Burnett .................. A61F 2/07 623/1.36 |
| 2009/0138071 A1 | 5/2009 | Cheng et al. |
| 2009/0177215 A1 | 7/2009 | Stack et al. |
| 2009/0187230 A1 | 7/2009 | Dilorenzo |
| 2009/0240340 A1 | 9/2009 | Levine et al. |
| 2009/0248171 A1 | 10/2009 | Levine et al. |
| 2009/0270818 A1 | 10/2009 | Duke |
| 2010/0010298 A1 | 1/2010 | Bakos et al. |
| 2010/0030017 A1 | 2/2010 | Baker et al. |
| 2010/0114124 A1 | 5/2010 | Kelleher et al. |
| 2010/0114130 A1 | 5/2010 | Meade et al. |
| 2010/0256775 A1 | 10/2010 | Belhe et al. |
| 2010/0280313 A1 | 11/2010 | Gasche et al. |
| 2010/0305590 A1 | 12/2010 | Holmes et al. |
| 2011/0004146 A1 | 1/2011 | Priplata et al. |
| 2011/0009690 A1 | 1/2011 | Belhe et al. |
| 2011/0092761 A1* | 4/2011 | Almog .................. A61M 25/09 600/16 |
| 2011/0264234 A1 | 10/2011 | Baker et al. |
| 2012/0053653 A1 | 3/2012 | Hiernaux et al. |
| 2012/0083871 A1 | 4/2012 | Ryan |
| 2012/0095497 A1 | 4/2012 | Babkes et al. |
| 2012/0191213 A1 | 7/2012 | Baker et al. |
| 2012/0191215 A1 | 7/2012 | Baker et al. |
| 2012/0203061 A1 | 8/2012 | Birk |
| 2012/0310138 A1* | 12/2012 | Behan ...................... A61F 2/04 604/9 |
| 2012/0310327 A1 | 12/2012 | McHugo |
| 2013/0123811 A1 | 5/2013 | Baker et al. |
| 2013/0217957 A1* | 8/2013 | Maahs ............... A61B 17/0487 600/37 |
| 2013/0296913 A1 | 11/2013 | Foote et al. |
| 2013/0324902 A1 | 12/2013 | Miller et al. |
| 2014/0031841 A1* | 1/2014 | DeVries ............ A61B 17/0644 606/151 |
| 2014/0135799 A1 | 5/2014 | Henderson |
| 2014/0158747 A1 | 6/2014 | Measamer et al. |
| 2014/0277341 A1 | 9/2014 | Havel et al. |
| 2015/0039092 A1 | 2/2015 | Baker et al. |
| 2015/0182239 A1 | 7/2015 | Baker et al. |
| 2016/0151233 A1 | 6/2016 | Baker et al. |
| 2016/0228268 A1 | 8/2016 | Hingston et al. |
| 2017/0172723 A1 | 6/2017 | Foote et al. |
| 2018/0104080 A1 | 4/2018 | Baker et al. |
| 2018/0235794 A1 | 8/2018 | Kagen et al. |
| 2019/0298560 A1 | 10/2019 | Belhe et al. |

FOREIGN PATENT DOCUMENTS

| | | |
|---|---|---|
| EP | 0760696 B1 | 8/2001 |
| EP | 1808888 A2 | 7/2007 |
| EP | 2240215 B1 | 1/2014 |
| JP | 2660101 | 6/1997 |
| JP | 2006-103873 A | 4/2006 |
| JP | 2007508053 A | 4/2007 |
| JP | 2011509758 A | 3/2011 |
| RU | 2045233 C1 | 10/1995 |
| RU | 94026119 A | 8/1996 |
| RU | 2386455 | 4/2010 |
| WO | WO 93/22986 | 11/1993 |
| WO | WO 94/12136 | 6/1994 |
| WO | WO 01/35834 A1 | 5/2001 |
| WO | WO 01/85034 A1 | 11/2001 |
| WO | WO 02/060328 A1 | 8/2002 |
| WO | WO 02/094105 A2 | 11/2002 |
| WO | WO 2004/019826 A1 | 3/2004 |
| WO | WO 2004/064680 A1 | 8/2004 |
| WO | WO 2004/064685 | 8/2004 |
| WO | WO 2005/037152 | 4/2005 |
| WO | WO 2006/044640 A1 | 4/2006 |
| WO | WO 2006/078672 A1 | 7/2006 |
| WO | WO 2007/092390 A2 | 8/2007 |
| WO | WO 2008/100984 A2 | 8/2008 |
| WO | WO 2008/101048 A2 | 8/2008 |
| WO | WO 2008/101078 A2 | 8/2008 |
| WO | WO 2009/048398 A1 | 4/2009 |
| WO | WO 2009/091899 A2 | 7/2009 |
| WO | WO 2010/117641 A2 | 10/2010 |
| WO | WO 2011/056608 A1 | 5/2011 |
| WO | WO 2011/063307 A1 | 5/2011 |
| WO | WO 2011/089601 A1 | 7/2011 |
| WO | WO 2011/097209 A1 | 8/2011 |
| WO | WO 2011/116025 A1 | 9/2011 |
| WO | WO 2012/044917 A1 | 4/2012 |
| WO | WO 2012/136249 A1 | 10/2012 |
| WO | WO 2012/162114 A1 | 11/2012 |
| WO | WO 2013/090190 A1 | 6/2013 |
| WO | WO 2013/134227 A1 | 9/2013 |
| WO | WO 2014/141239 A1 | 9/2014 |
| WO | WO 2015/031077 A1 | 3/2015 |
| WO | WO 2016/109346 A1 | 7/2016 |
| WO | WO 2018/073752 A1 | 4/2018 |

(56) References Cited

FOREIGN PATENT DOCUMENTS

| WO | WO 2018/083632 A1 | 5/2018 | |
| WO | WO-2019009918 A1 * | 1/2019 | ......... A61B 17/1114 |

OTHER PUBLICATIONS

Andrew S. Lowe, M.D. and Maria B. Sheridan, M.D., "Esphogeal Stenting", Seminars in Interventional Radiology, vol. 21, No. 3, 2004, pp. 157-166.

"Polyflex® Espohageal Stent", Silicone Covered Stent, Boston Scientific, three pages (2003).

Andrew F.R. Dixon, Johgn B. Dixon, and Paul E. O'Brien, "Laparoscopic Adjustable Gastric Banding Induces Prolonged Satiety: A Randomized Blind Crossover Study", The Journal of Clinical Endocrinology & Metabolism, pp. 813-819, 2005.

Roman, S. et al., "Intragastric balloon for 'non-morbid' obesity: a retrospective evaluation of tolerance and efficacy," Obes. Surg., 2004, 14(4), 539-44, abstract, [on-line], [found Apr. 17, 2009, from Pubmed database].

Busetto, L. et al., "Preoperative weight loss by intragastric balloon in super-obese patients treated with laparoscopic gastric banding: a case-control study," Obes Surg., 2004, 14(5), 671-6, abstract, [on-line], [found Apr. 17, 2009, from Pubmed database].

Summary of Official Action dated Oct. 29, 2009, from the Israel Patent Office in a patent application corresponding to the present application.

Lowe, Andrew S., M.D. and Sheridan, Maria B., M.D., "Esophageal Stenting," annotated by Israel Patent Office (2004).

Abstract and claims of U.S. Pat. No. 6,960,233 annotated by the Israel Patent Office (Nov. 1, 2005).

Schembre, Drew, "Advances in Esophageal Stenting: the Evolution of Fully Covered Stents for Malignant and Benign Disease," Adv. Ther., Springer Healthcare, Apr. 1, 2010, pp. 1-13.

S. Fukudo, T. Nomura, M. Hongo, "Impact of corticotropin-releasing hormone on gastrointestinal motility and adrenocorticotropic hormone in normal controls and patients with irritable bowl syndrome", Jan. 19, 1998.

D.G. Maxton, D.F. Martin, P.J. Whorwell, M. Godfrey. "Abdominal distension in female patients with irritable bowel syndrome: exploration of possible mechanisms", Aug. 3, 1990.

Dixon et al. "Health Outcomes of Severely Obese Type 2 Diabetic Subjects 1 Year After Laparoscopic Adjustable Gastric Banding". 2002. Diabetic Care 25:358-363. (Year 2002).

International Search Report of the International Searching Authority from corresponding Patent Cooperation Treaty (PCT) Patent Application No. PCT/IB2020/052169, mailed Jul. 15, 2020.

European Search Report dated Nov. 7, 2022 for corresponding EP Application No. EP20769677.4.

* cited by examiner

SINGLE MEMBER INTRALUMINAL DEVICE AND METHOD OF FIXATION

BACKGROUND OF THE INVENTION

The present invention is directed to a method and structure for resisting migration of an intraluminal device in a lumen and in particular to a single member intraluminal device that is fixed to a portion of the gastrointestinal (GI) tract. While it may be used in other portions of the GI tract, the invention is illustrated with a single member intraluminal device fixed to the cardiac portion of the stomach or adjacent the gastro-esophageal (EG) junction.

SUMMARY OF THE INVENTION

The embodiments of the present invention are useful for fixation of an intraluminal device such as a bariatric device and method as disclosed in commonly assigned U.S. Pat. No. 9,198,789 and international application publication WO 2016/109346 or as a metabolic disease treatment device and method as disclosed in commonly assigned international application publication WO 2015/031077, the disclosures of which are hereby incorporated herein by reference. Other applications will be apparent to the skilled artisan.

A particularly difficult problem is to fix a generally planar member, such as a cardiac member in the applications set forth above, to the inner wall of a lumen, particularly one that experiences peristalsis, such as the cardiac portion of the stomach. While other solutions are known in the art, the embodiments of the present invention allow fixation of a planar member involving just the member itself.

An intraluminal device and method of deploying an intraluminal device in a portion of a lumen includes a body having a wall defining a surface, the surface configured to a portion of a lumen and an anchor system. The anchor system is configured to fix the body to an inner wall of the lumen in a manner that said surface is adapted to apply at least intermittent pressure to the inner wall of the lumen. The anchor system includes a tissue fold that is adjacent the wall. The tissue fold transmits a force between the inner wall of the lumen and the body. The method includes forming a tissue fold of the inner wall of the lumen, the tissue fold being adjacent the body wall, the tissue fold transmitting a force between the inner wall of the lumen and said body.

The anchor system may be a plurality of anchors, each comprising a fastener that is adapted to retain the wall with the tissue fold of the lumen that is adjacent the wall. Each of the anchors may comprise at least one opening in the wall and a crossbar at an edge portion of the at least one opening, the tissue fold positioned in the at least one opening. At least one opening may be provided at an edge portion of the body. Each of the anchors may include an opening traversed by a crossbar, with a tissue fold of the lumen extending into the opening on opposite sides of the crossbar and the fastener adapted to couple the tissue folds in a manner that retains the crossbar between the tissue folds. The crossbar may be retained between the tissue folds by fastening the tissue folds together. The tissue folds may be fastened together by a mechanical fastener, a suture or the like. The anchor may be a tissue fold extending into an opening and a clip that is larger than the opening grasping the tissue fold in order to retain the tissue fold in the opening.

The wall may have a central opening and a peripheral edge and the anchors spaced from both the central opening and peripheral edge. The anchor may be adapted to be disabled in order to explant the body from the lumen. The anchor may be adapted to be disabled by cutting the fastener or by removing the crossbar from adjacent the opening. The crossbars may be adapted to be removed together by being interconnected in a crossbar assembly. The crossbars may be removed together by being attached at one end with a removable attachment with the wall and have a grasping portion at an opposite end.

The surface may be adapted to apply an adjustable pressure to the inner wall of the lumen. The surface may be moveable with an inner bladder and a control system adjusting inflation of the inner bladder. The control system may include a controller and an outer bladder on an opposite side of the wall, with the controller adapted to exchange a fluid between the bladders in order to move said surface. The body may be configured to the cardiac portion of the stomach and anther body connected with the body adapted to be in a distal portion of the esophagus. The anchor system may include the other body may be connected with the tissue fold and with a controller on the wall. The control system may include a controller on the wall that is connected with the tissue fold with a filament to transmit a force between said tissue fold and the wall. The controller may be adapted to adjust a length of the filament to adjust a force between the body and the tissue fold to adjust pressure applied by the surface to the inner wall of the lumen.

DESCRIPTION OF THE PREFERRED EMBODIMENTS

Figure 1:
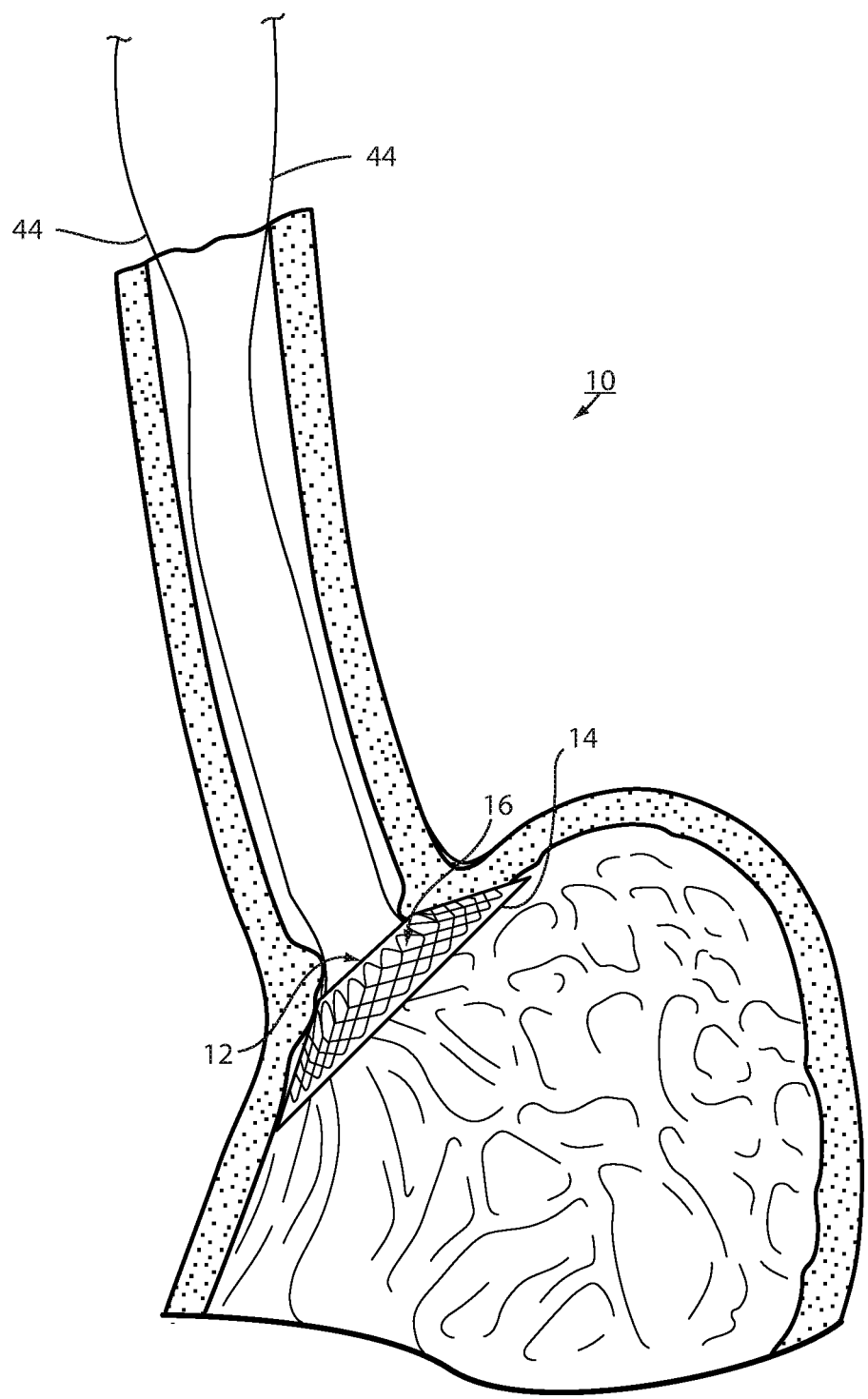
FIG. 1 is an elevational view of an intraluminal device according to embodiments of the invention deployed to a recipient.

The present invention will now be described with reference to the accompanying figures, wherein the numbered elements in the following written description correspond to like-numbered elements in the figures.

Referring now to the drawings and the illustrative embodiments depicted therein, an intraluminal device 10 includes a body 12 made up of a flat pattern, such as a weave, of a filament made of nitinol wire, plastic filament, carbon filament or the like, covered with bio-compatible layers such as silicone, thereby defining a wall 14 having a surface 16 that is configured to a portion of the lumen. In the illustrated embodiment, body 12 is configured to apply pressure to the cardiac portion of the stomach and has a central opening 15 that is adapted to be aligned with the EG sphincter in order to pass food through opening 15. Body 12 has an outer edge portion 28 that is shown as circular so that surface 16 generally covers the inner wall 18 of the lumen, such as the cardiac portion of the stomach. Other shapes can be used.

An anchor system 20 which, alone or in combination with another anchoring technique, is configured to fix body 12 to inner wall 18 of the lumen. It does so in a manner that surface 16 is capable of applying at least intermittent pressure to inner wall 18 of the lumen. Anchor system 20 is made up of a plurality of anchors 25. Each anchor 25 includes a fastener 22 that is capable of at least partially retaining wall 18 with a tissue fold 24 of the lumen that is adjacent to wall 18.

Figure 3:
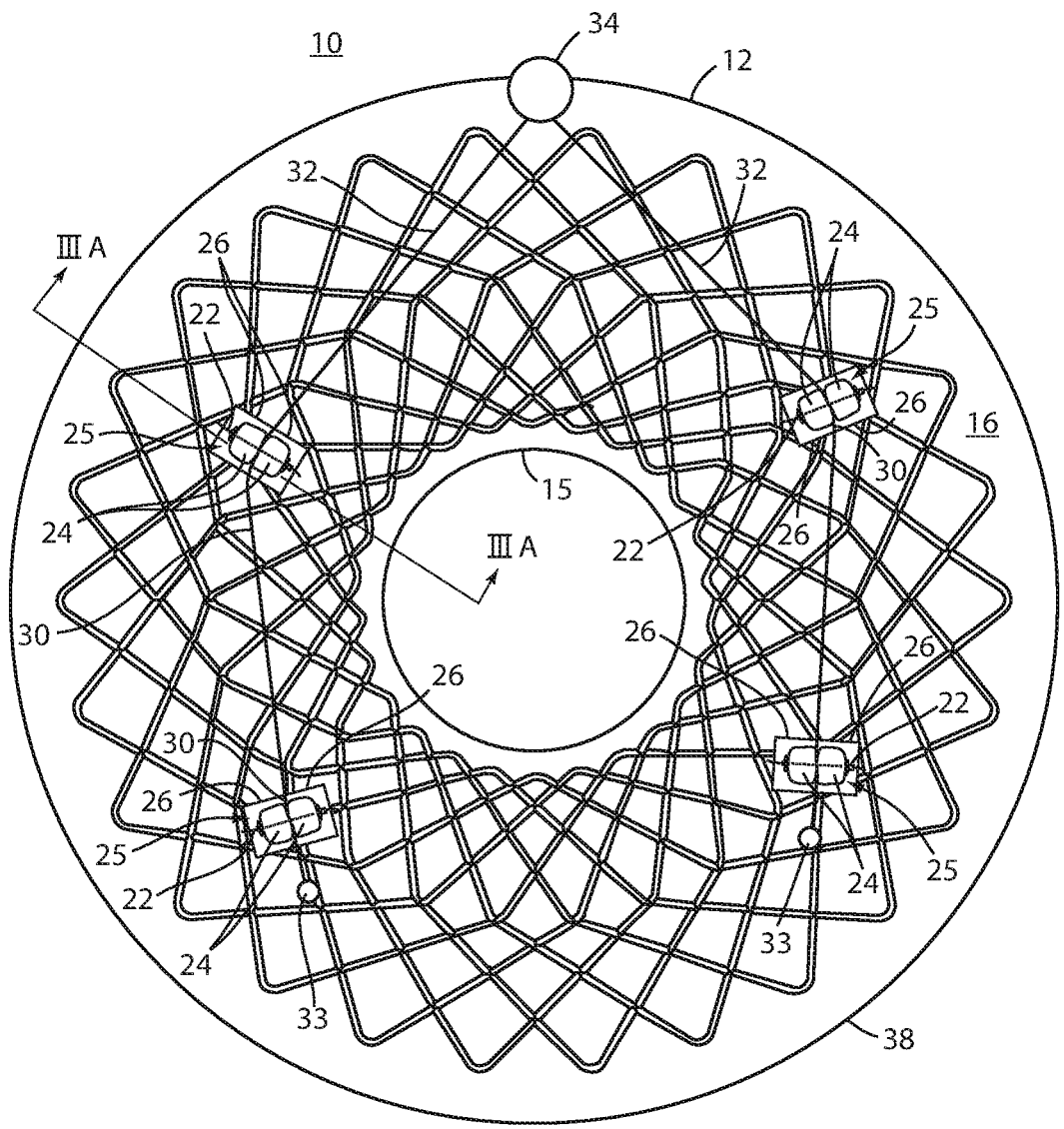
FIG. 3 is a view of the intraluminal device in FIG. 1 taken from the direction III-III in FIG. 2.
Figure 3A:
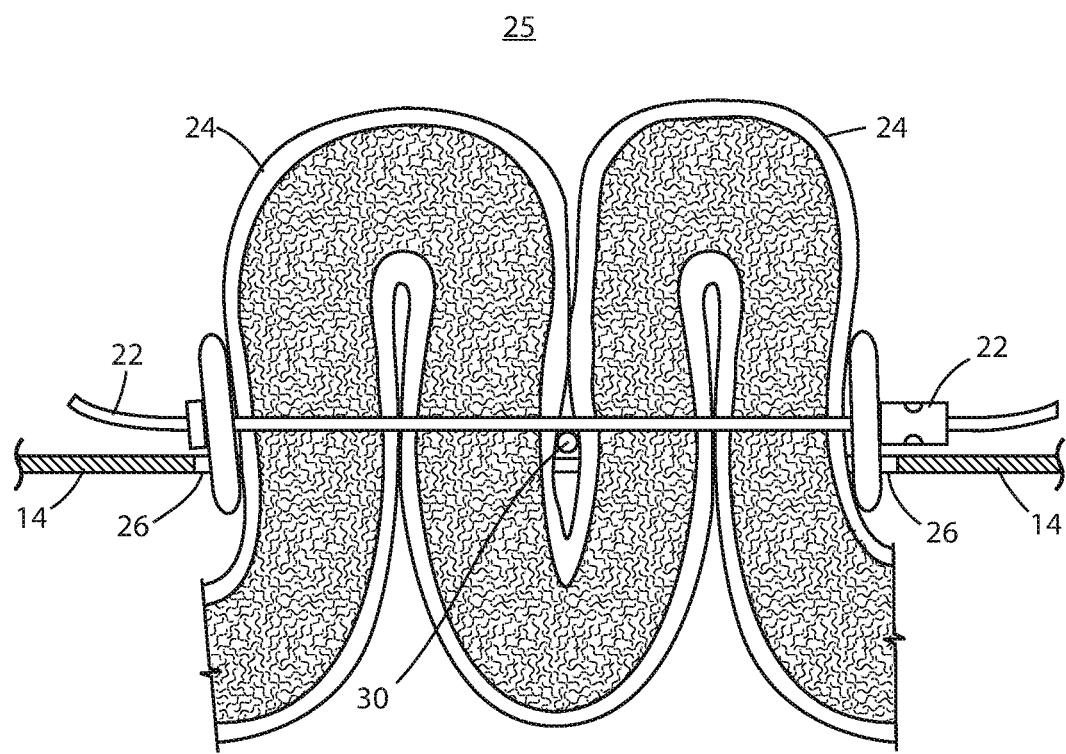
FIG. 3A us a sectional view taken along the lines IIIa-IIIa in FIG. 3.

In the embodiment illustrated in FIG. 3*a*, each anchor 25 is made up of an opening 26 that is traversed by a crossbar 30 bisecting opening 26. With a pair of tissue folds 24 of the lumen extending into each opening 26, a fastener 22 couples the tissue folds 24 in a manner that retains crossbar 30 between the tissue folds. In the illustrated embodiment, 4 anchors are spaced from both central opening 15 and peripheral edge portion 38 of wall 14. This evenly distributes the pressure applied by surface 16 to inner wall 18 of the lumen. Of course, a greater or fewer number of anchors 25 can be distributed generally evenly about central opening 15 in wall 18. Tissue folds 24 may be formed and pulled into opening 26 and fastener 22 may be deployed according to the principles set forth in U.S. Pat. No. 10,172,608, the disclosure of which is hereby incorporated herein by reference. The first tissue fold is formed and pulled into opening 26 then retained by passing fastener 22 through that fold. The second tissue fold is then formed and pulled into opening 26 on the other side of crossbar 30 and fastened with the other tissue fold by passing the same fastener 22 through the second tissue fold. Other endoscopic fastener devices may be used such as a full-bite suturing device from Apollo Endosurgical and the like. Alternatively, a single tissue fold may be formed and pulled through opening 26 and retained in the opening by a mechanical clip that is larger in size than the opening.

The anchors 25 are adapted to be disabled in order to explant body 12 from the lumen. In the embodiment illustrated in FIG. 3, anchors 25 can be disabled by the crossbar 30 of each anchor being able to be removed from between openings 26. Crossbars 30 can be interconnected in a crossbar assembly 32 so they can be removed together and thereby defeat anchor system 20 in order to explant body 12. Crossbar assembly 32 can be removed by being attached at one end with a removable attachment 33 with wall 14 and having a grasping portion 34 at an opposite end of the crossbar assembly. Removable attachment 33 can be a suture or the like and holds crossbar assembly 32 in place during deployment in the lumen. When attachment 33 is severed, such as with an endoscopic scissor or other cutting implement, the crossbar assembly can be axially withdrawn from each anchor 25 by grasping portion 34 with an endoscopic tool and pulling on the crossbar assembly. This axially withdraws crossbar 30 from each anchor 25. Grasping portion 34 may be an enlarged area such as a bead, loop, or the like. Crossbar assembly 32 including crossbars 30, removable attachment 33 and grasping portion 34 are assembled to body 12 prior to deployment of the intraluminal device in the lumen with anchors 25 completed after deployment of the body in the lumen.

Figure 2:
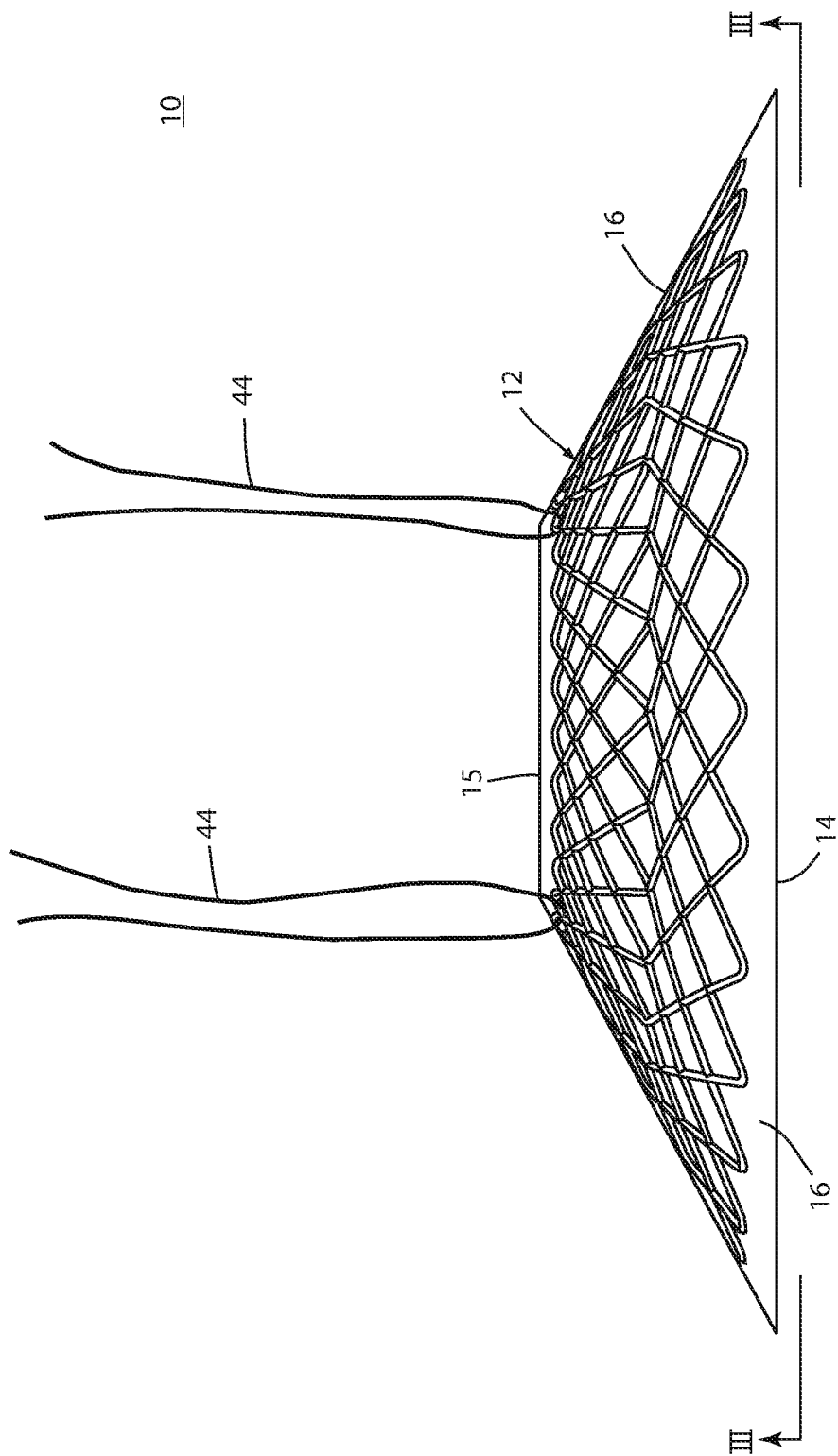
FIG. 2 is an elevation view of the intraluminal device in FIG. 1.

In order to deploy intraluminal device 10, body 12 is deployed to the stomach with a deployment device of the type disclosed in commonly assigned U.S. Pat. No. 9,545, 326, the disclosure of which is hereby incorporated herein by reference. Central opening 15 is aligned with the esophageal gastric junction using the deployment device traversing the EG junction and opening 15. Retention filaments 44 extending from wall 14 to external the recipient, as shown in FIGS. 1 and 2, can be used to retain wall 14 to the cardiac portion of the stomach of the recipient during deployment. Retention filaments 44 are looped around an opening in wall 14 so they may be withdrawn following deployment by pulling on one filament of the loop.

Figure 4:
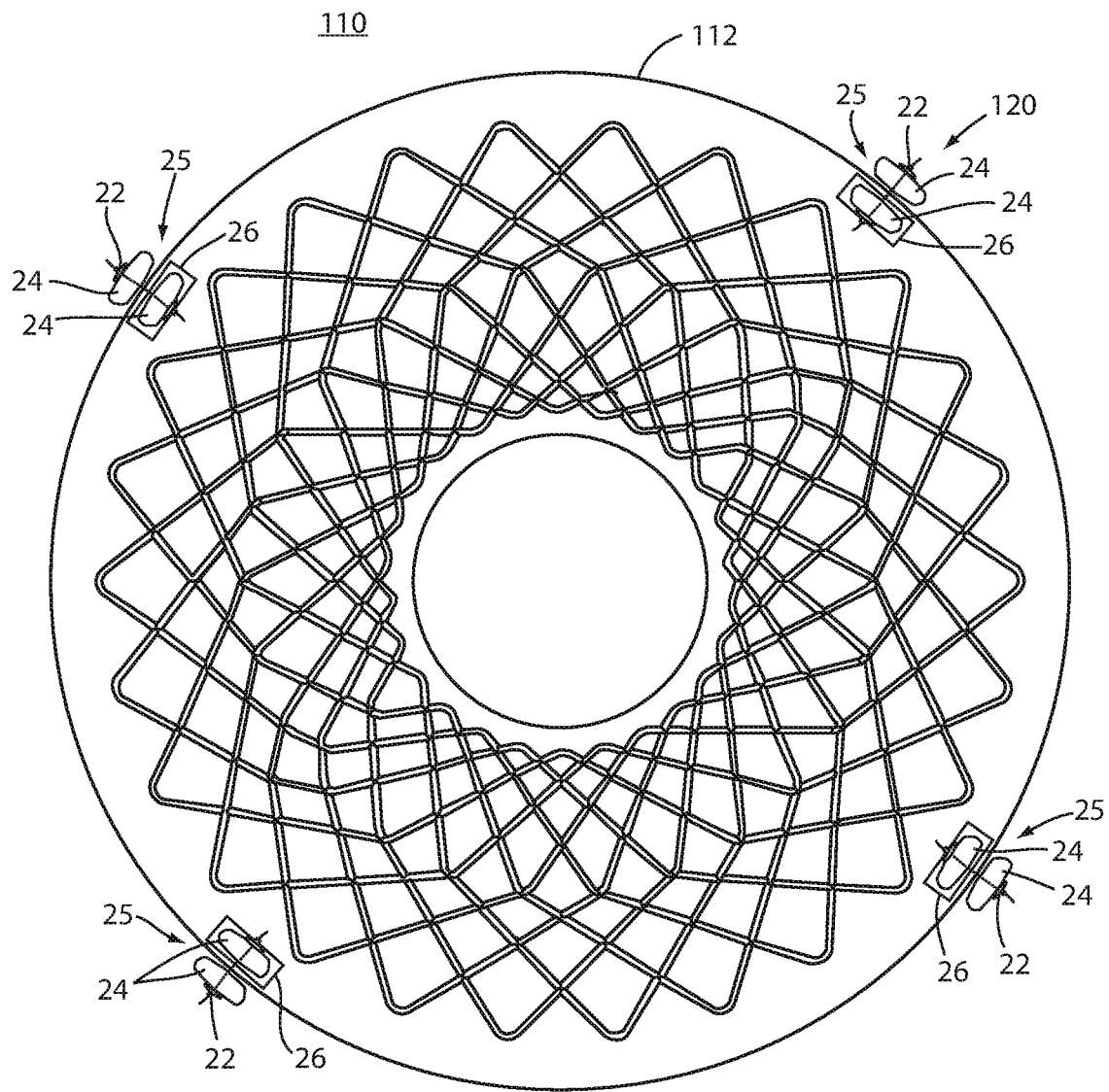
FIG. 4 is the same view as FIG. 3 of an alternative embodiment.

In the alternative embodiment illustrated in FIG. 4, intraluminal device 110 includes a body 112 anchored to the inner wall of the lumen with an anchor system 120 made up of anchors 25 with at least one opening 26 in wall 14 and an optional crossbar 30 (not shown in FIG. 4) at an edge portion of opening 26. A tissue fold 24 is positioned in opening 26 and anther tissue fold 24 outside of edge portion 28 of wall 14. If a cross bar is used with each anchor 25 they can be joined in a cross bar assembly 22 as previously described with respect to intraluminal device 10. If no cross bar is used, then the anchor can be disabled by severing fastener 22.

Figure 5:
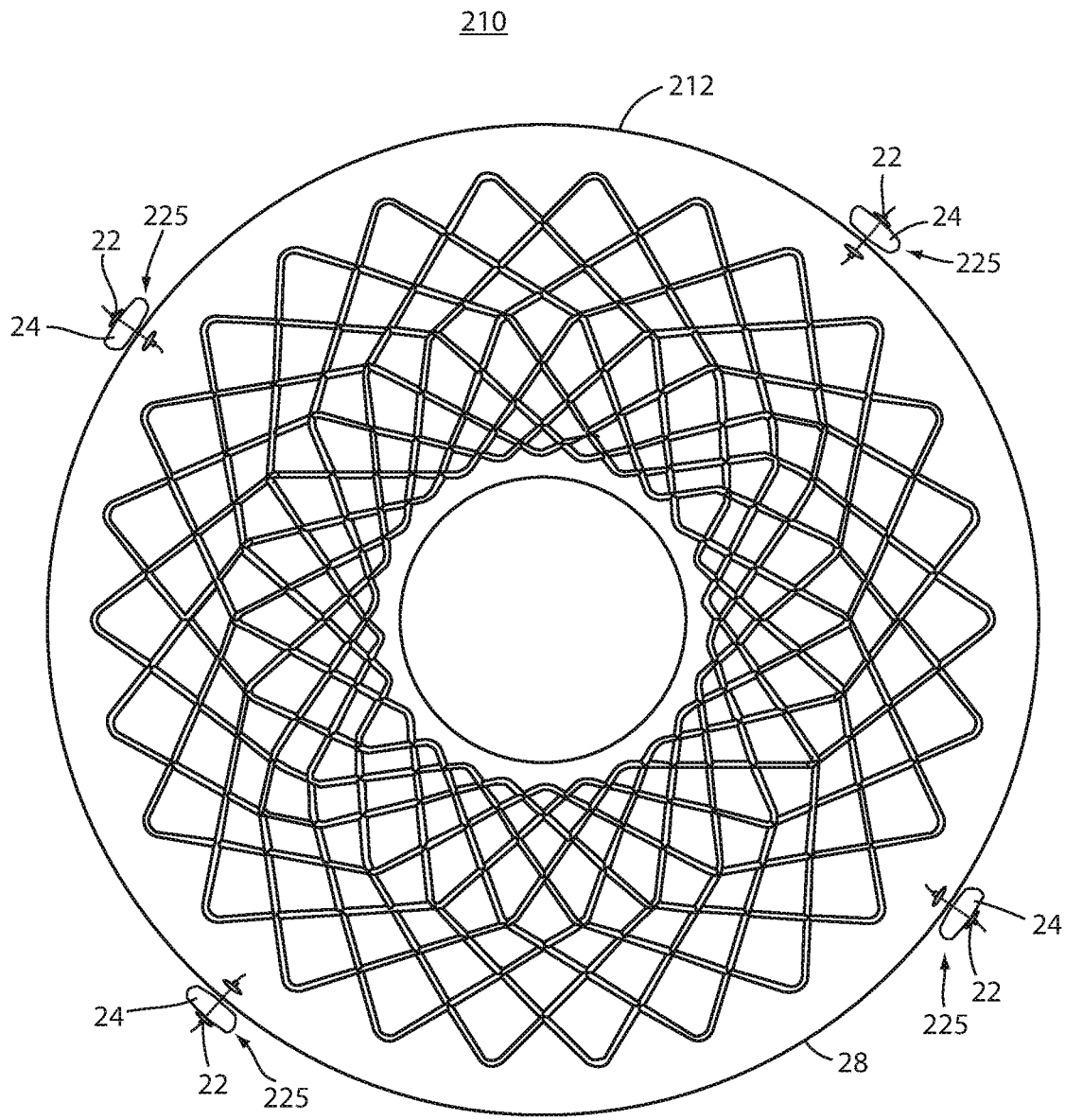
FIG. 5 is the same view as FIG. 3 of another alternative embodiment.

In the alternative embodiment illustrated in FIG. 5, intraluminal device 210 includes a body 212 with no opening provided in wall 14. Each anchor 225 includes a tissue fold 24 outside of edge portion 28 of wall 14 that is connected directly to wall 14 with a fastener 22 that penetrates the tissue fold 24 and the wall 14. The anchor 225 can be disabled by severing fastener 22.

Figure 6:
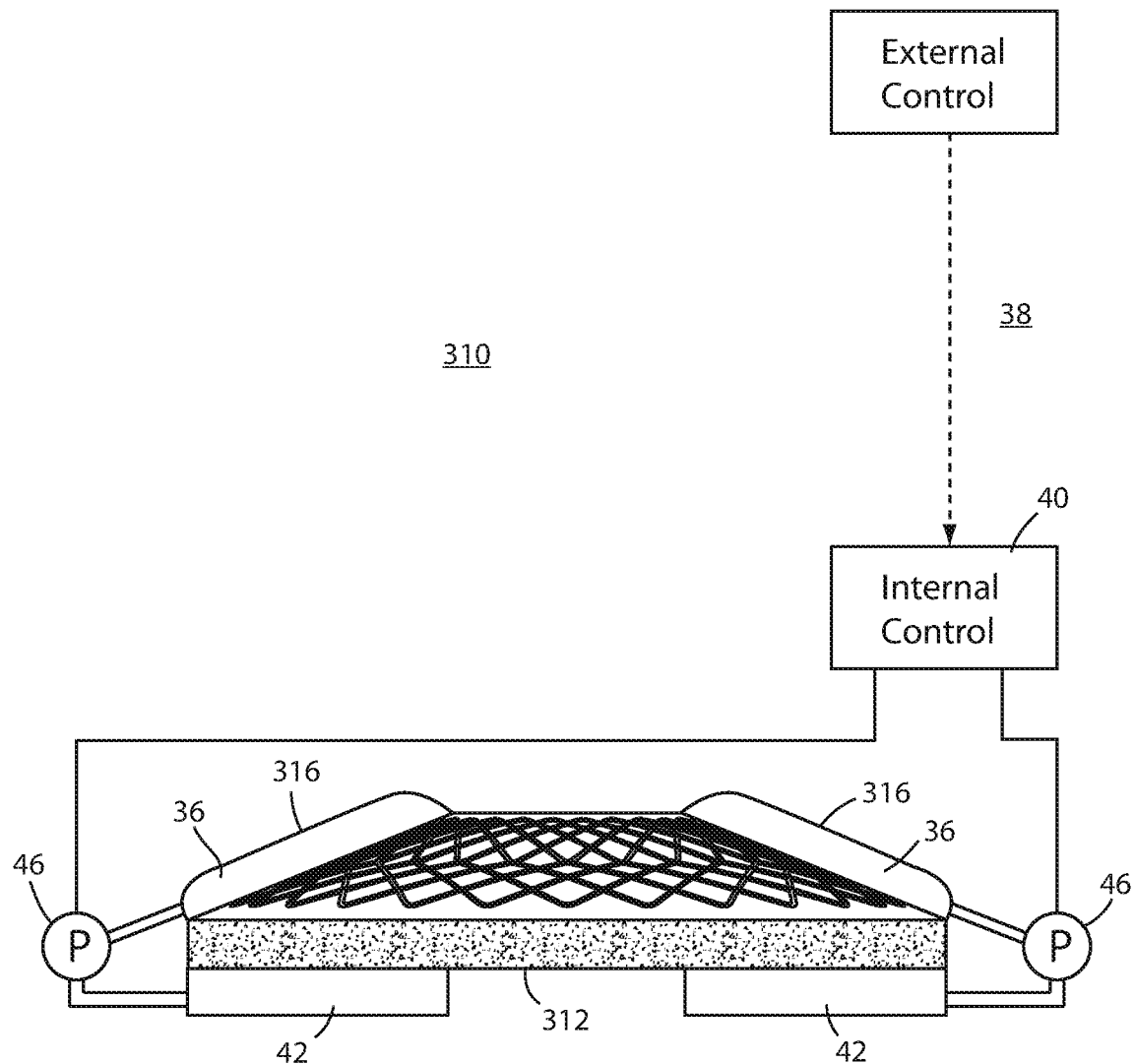
FIG. 6 is the same view as FIG. 3 of an embodiment of an intraluminal device capable of applying adjustable pressure to the lumen wall.

An intraluminal device 310 illustrated in FIG. 6 is capable of applying an adjustable pressure with surface 316 of a body 312 to the inner wall of the lumen. Surface 316 is moveable with one or more inner bladders 36 and a control system 38 that adjusts inflation of inner bladder(s) 36 using a controller 40 and one or more outer bladders 42 on an opposite side of wall 14. Controller 40 exchanging a fluid between bladders 36 and 42 using pumps 46 in order to move surface 316 toward and away from the inner wall of the lumen.

Figure 7:
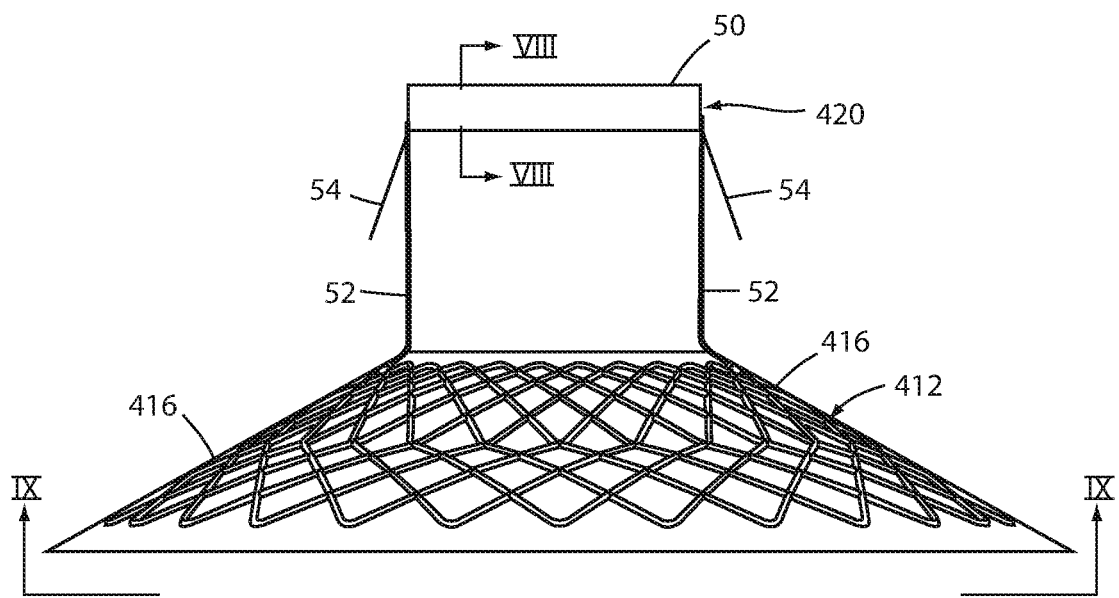
FIG. 7 is an elevation view of an intraluminal device according to an alternative embodiment of an intraluminal device.
Figure 8:
FIG. 8 is a sectional view taken along the lines VIII-VIII in FIG. 7.
Figure 9:
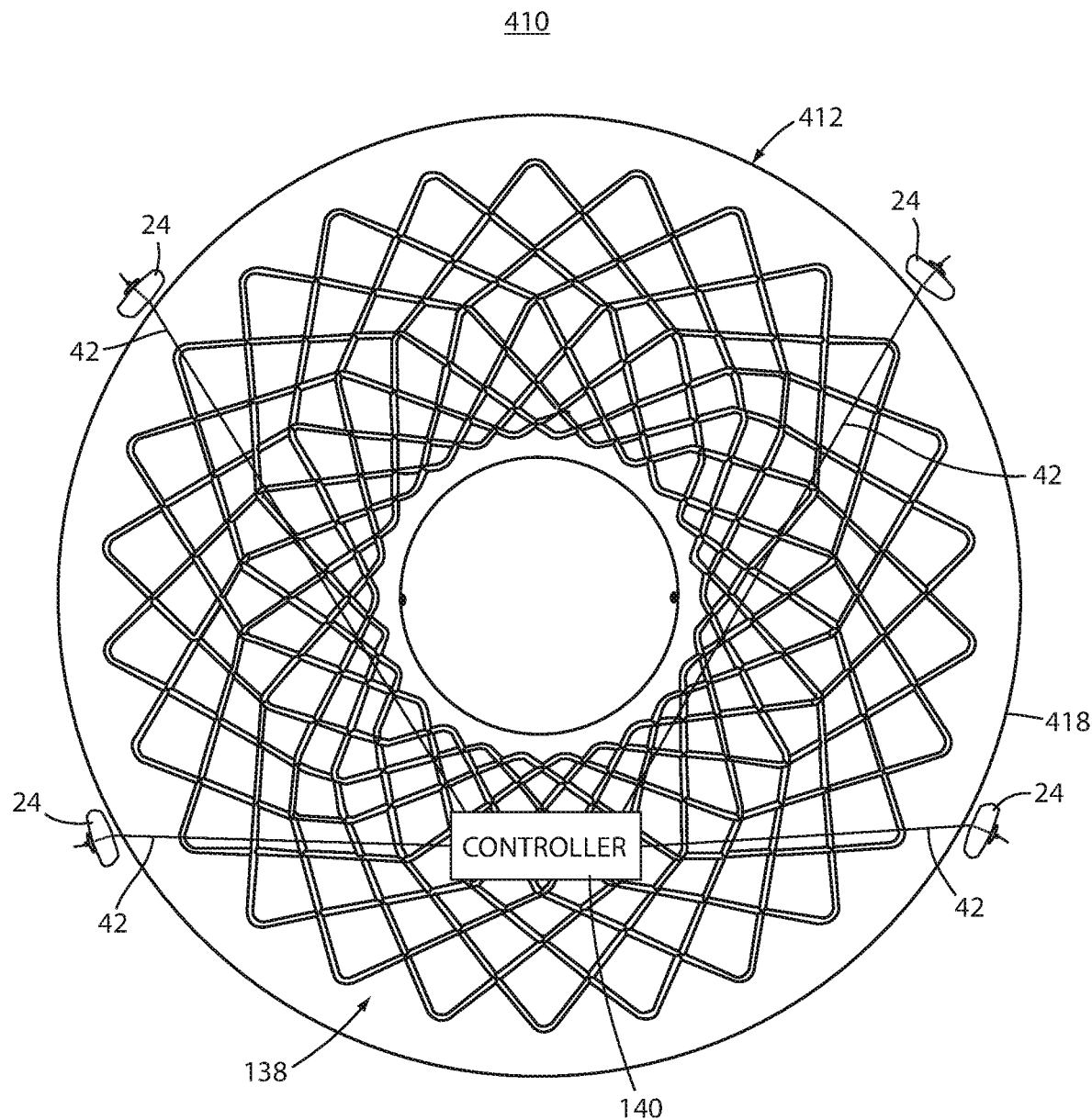
FIG. 9 is a bottom plan view taken from the direction IX-IX in FIG. 7.

Another embodiment of an intraluminal device 410 includes a body 412 having a surface 416 that applies at least intermittent pressure to the inner wall of the lumen. As seen in FIG. 7, device 410 utilizes another body 50 and two or more connectors 52 connecting with body 412 as an additional anchor system 420 to help fix body 412 to a portion of a lumen. Body 412 is configured to the size and shape of the cardiac portion of the stomach and another body 50 is configured to the size and shape of the distal portion of the esophagus. Another body 50 may be anchored in the distal esophagus using various techniques disclosed in the art by the present inventor. In the illustrated embodiment, anchor system 420 utilizes at least one distally directed tine 54 that at least partially penetrates the esophageal-gastric junction in the manner disclosed in commonly assigned patent application U.S. Ser. No. 62/823,259, entitled INTRALUMINAL DEVICE AND METHOD WITH ANTI-MIGRATION, filed Mar. 25, 2019 the disclosure of which is hereby incorporated herein by reference. Connectors 52 cause body 412 to apply at least an intermittent force to the cardiac portion of the stomach with surface 416. Another body 50 may have a generally curvilinear cross section as illustrated in FIG. 8, in order to minimize potential for irritating the esophagus, or some other shape. Alternatively, intraluminal device 410 may utilize another body 50 and connectors 52 just to provide an alignment of its center opening 15 with the esophagus. This ensures that food and other intraluminal content pass body 412 without any interference. Also, body 50 and connectors 52 retain the axial orientation of body 412. In such alternative embodiment, tines 54 are absent as no additional fixation is provided by body 50 and connectors 52.

With intraluminal device 410 anchored against the inner wall of the cardiac portion of the stomach, a plurality of tissue folds 24 are a part of control system 138. Control system 138 includes a controller 140 that is attached to the inner surface of body 412 and is connected with tissue folds 24 with filaments 42. Controller 140 adjusts pressure applied by surface 416 to the cardiac portion of the stomach by adjusting the length of filaments 42. As the opposite end of filaments 42 are joined with the inner wall of the cardiac portion of the stomach with tissue folds 24, the shortening of filaments 42 by controller 140 causes distortion on wall 412 such as by warping or rolling which causes the pressure applied by surface 416 to change. Increasing the length of filaments 24 has the opposite affect. Thus in intraluminal device 410 tissue folds 24 are primarily concerned with control of the amount of pressure applied to the cardiac portion of the stomach than to anchoring of the device body. Other applications of tissue folds will be apparent to the skilled artisan in view of the disclosures herein.

Embodiments of the invention may be used to provide fixation for use with the technology disclosed in commonly assigned U.S. Pat. No. 9,055,998 the disclosure of which is hereby incorporated herein by reference. Several of the embodiments disclosed in the '998 patent include single member intraluminal devices which could make use of the fixation techniques provided herein to provide sole or additional fixation of the intraluminal devices in the lumen of the recipient.

While the foregoing description describes several embodiments of the present invention, it will be understood by those skilled in the art that variations and modifications to these embodiments may be made without departing from the spirit and scope of the invention, as defined in the claims below. The present invention encompasses all combinations of various embodiments or aspects of the invention described herein. It is understood that any and all embodiments of the present invention may be taken in conjunction with any other embodiment to describe additional embodiments of the present invention. Furthermore, any elements of an embodiment may be combined with any and all other elements of any of the embodiments to describe additional embodiments.

The invention claimed is:

1. An intraluminal device, comprising:
a body having a wall defining a surface, said surface configured to a portion of a lumen;
an anchor system, said anchor system configured to fix said body to an inner wall of the lumen in a manner that said surface is adapted to apply at least intermittent pressure to the inner wall of the lumen;
wherein said anchor system comprises a plurality of anchors, each comprising a fastener that is adapted to retain said wall with at least two tissue folds of the lumen that are adjacent the wall; and
wherein each of said anchors comprises an opening traversed by a crossbar, said opening adapted to receive the at least two tissue folds of the lumen extending into the opening on opposite sides of the crossbar and said fastener adapted to couple the at least two tissue folds in a manner that retains the crossbar between the at least two tissue folds.

2. The device as claimed in claim 1 wherein said wall has a central opening and a peripheral edge and wherein said anchors are spaced from both said central opening and said peripheral edge.

3. The device as claimed in claim 1 wherein said anchor is adapted to be disabled in order to explant the body from the lumen.

4. The device as claimed in claim 3 wherein said anchor is adapted to be disabled by cutting the fastener.

5. The device as claimed in claim 3 wherein said anchor is adapted to be disabled by said crossbar being adapted to be removed from between the tissue folds.

6. The device as claimed in claim 5 wherein a plurality of said crossbars are adapted to be removed together by being interconnected in a crossbar assembly.

7. The device as claimed in claim 6 wherein said crossbars are adapted to be removed together by being attached at one end with a removable attachment with said wall and having a grasping portion at an opposite end.

8. The device as claimed in claim 1 wherein said surface is adapted to apply an adjustable pressure to the inner wall of the lumen.

9. The device as claimed in claim 8 wherein the surface is moveable with an inner bladder and a control system adjusting inflation of said inner bladder.

10. The device as claimed in claim 9 wherein said control system includes a controller and an outer bladder on an opposite side of said wall, said controller exchanging a fluid between said bladders in order to move said surface.

11. The device as claimed in claim 8 including a controller on said wall that is adapted to connect the tissue fold with a filament and adapted to transmit a force between said tissue fold and said wall, said controller adapted to adjust a length of said filament to adjust a force between said body and said tissue fold to adjust pressure applied by the surface to the inner wall of the lumen.

12. The device as claimed in claim 1 wherein said anchor system includes another body that is connected with said body.

13. The device as claimed in claim 12 wherein said body is configured to the cardiac portion of the stomach and said anchor system comprises said another body adapted to be fixed to a distal portion of the esophagus.

14. A method of deploying an intraluminal device in a portion of a lumen, said method comprising:
said intraluminal device having a body with a wall defining a surface, said surface configured to a portion of a lumen;
an anchor system;
fixing said body to an inner wall of the lumen with said anchor system and applying at least intermittent pressure with said surface to the inner wall of the lumen; and
forming a tissue fold of the inner wall of the lumen, the tissue fold being adjacent the wall, said tissue fold transmitting a force between the inner wall of the lumen and said body;
wherein said anchor system comprises a plurality of anchors, said fixing said body including retaining said wall with the tissue fold of the lumen; and
wherein each of said anchors comprises an opening traversed by a crossbar, including forming at least two tissue folds of the lumen each extending into said opening on opposite sides of said crossbar and coupling the at least two tissue folds with a fastener in a manner that retains the crossbar between the tissue folds.

15. The method as claimed in claim 14 including explanting the body by disabling said anchor, wherein said anchor is disabled by removing said crossbar from between the tissue folds.

\* \* \* \* \*